(12) United States Patent
Aumuller et al.

(10) Patent No.: US 6,508,648 B2
(45) Date of Patent: *Jan. 21, 2003

(54) ABRASION DEVICE

(75) Inventors: Paul M. Aumuller, Richmond Hill; Paolo Accettone, Pickering, both of (CA)

(73) Assignee: IX Research Ltd., Richmond Hill (CA)

( * ) Notice: Subject to any disclaimer, the term of this patent is extended or adjusted under 35 U.S.C. 154(b) by 23 days.

This patent is subject to a terminal disclaimer.

(21) Appl. No.: 09/834,130

(22) Filed: Apr. 12, 2001

(65) Prior Publication Data

US 2001/0021496 A1 Sep. 13, 2001

Related U.S. Application Data

(63) Continuation-in-part of application No. 09/419,478, filed on Oct. 15, 1999, now Pat. No. 6,309,217.
(60) Provisional application No. 60/253,902, filed on Nov. 29, 2000.

(51) Int. Cl.[7] .................................................. A61C 3/02
(52) U.S. Cl. ....................................................... 433/88
(58) Field of Search ............................. 433/88, 80, 115, 433/116

(56) References Cited

U.S. PATENT DOCUMENTS

| 2,324,250 | A | * | 7/1943 | Voerge | |
|---|---|---|---|---|---|
| 3,972,123 | A | * | 8/1976 | Black | |
| 4,174,571 | A | * | 11/1979 | Gallant | |
| 4,412,402 | A | * | 11/1983 | Gallant | |
| 4,676,749 | A | * | 6/1987 | Mabille | 433/88 |
| 4,696,644 | A | * | 9/1987 | Goof | 433/88 |
| 4,950,160 | A | * | 8/1990 | Karst | 433/88 |
| 4,984,984 | A | * | 1/1991 | Esrock | 433/88 |
| 5,120,219 | A | * | 6/1992 | De Farcy | 433/88 |
| 5,334,019 | A | * | 8/1994 | GoldSmith et al. | 433/88 |
| 5,547,376 | A | * | 8/1996 | Harrel | 433/116 |
| 5,967,779 | A | * | 10/1999 | Brassil et al. | 433/88 |

* cited by examiner

Primary Examiner—Ralph A. Lewis

(57) ABSTRACT

An abrasion device is disclosed, which utilizes abrasive dust as abrasive material, and which provides for effective dust suppression through the use of a liquid-gas aerosol spray. The device consists of a means for the emission of a stream of the abrasive material. A spray of gas-liquid aerosol is also emitted from the device in a manner which effectively controls widespread contamination by the emitted abrasive material.

21 Claims, 14 Drawing Sheets

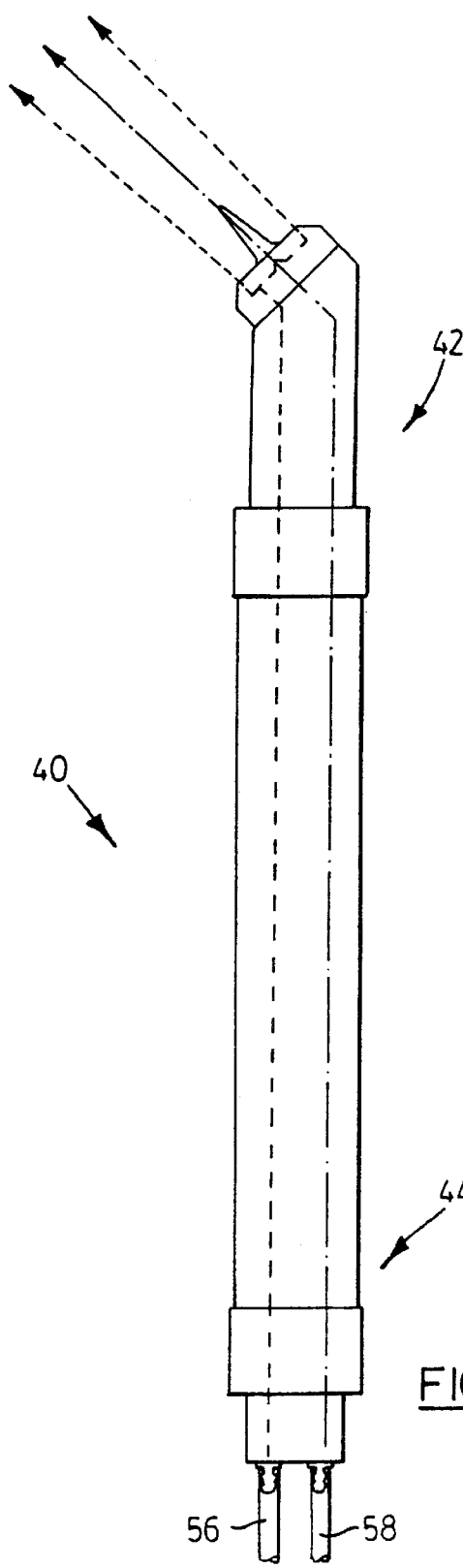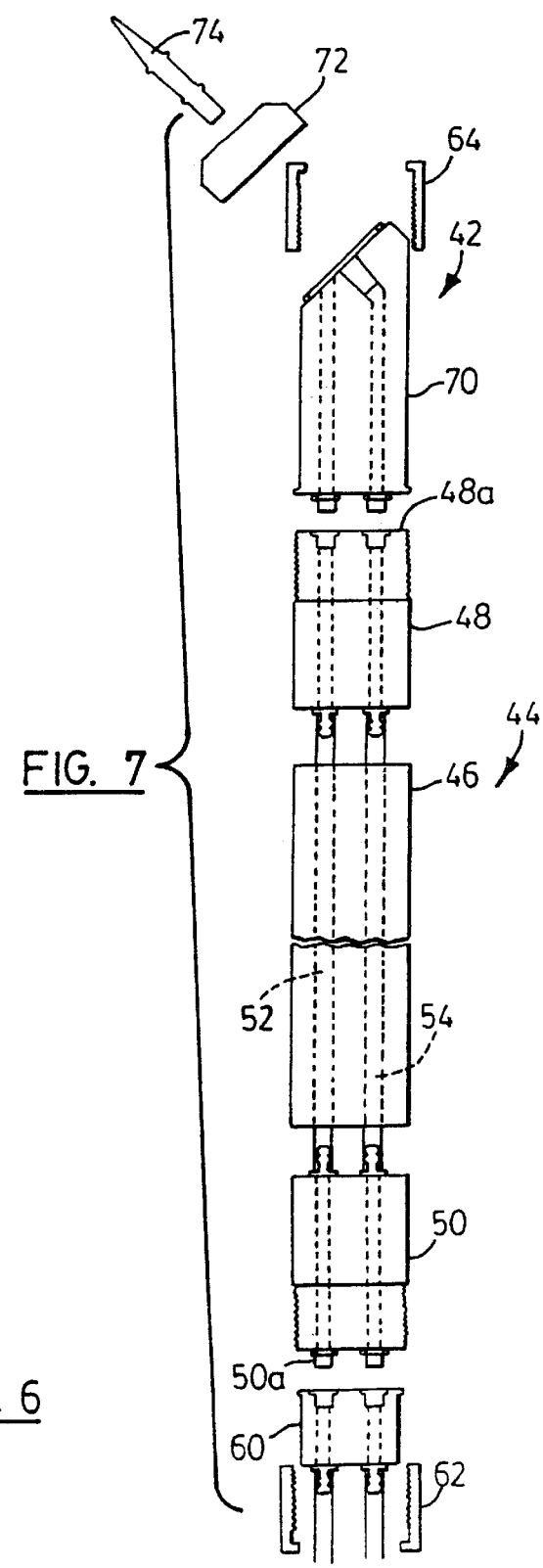

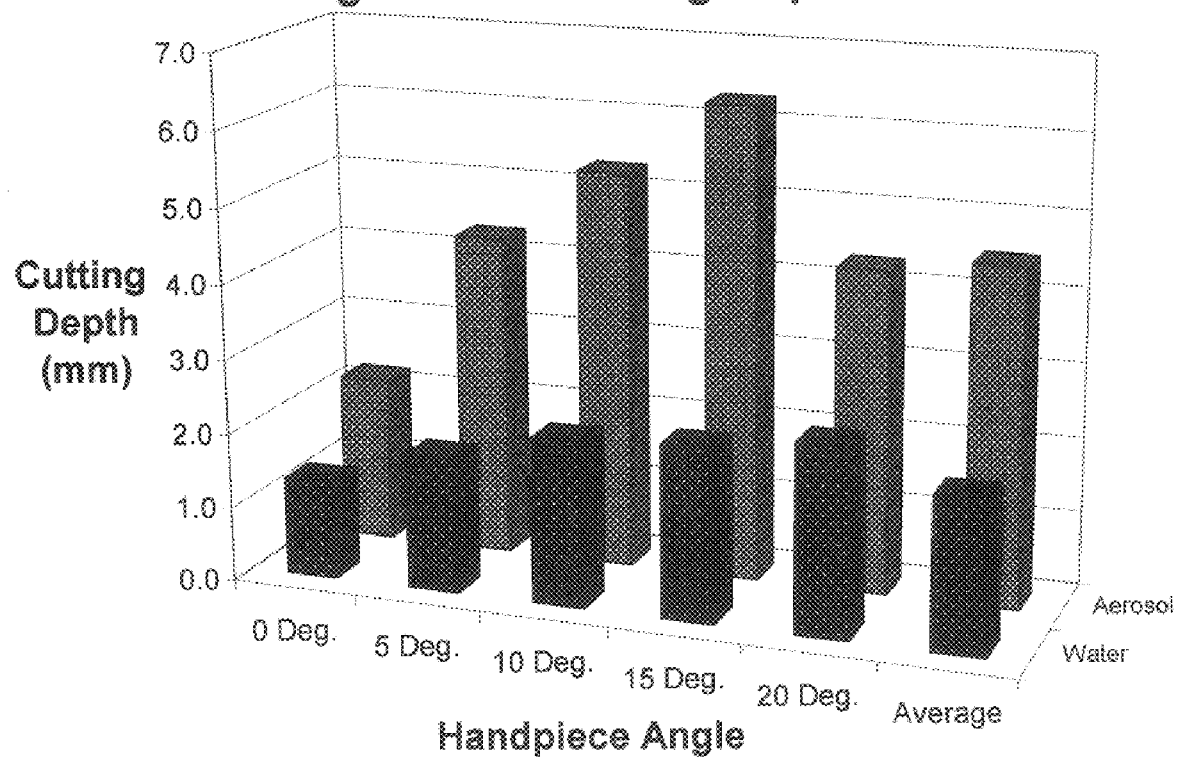

ABRASION DEVICE

REFERENCE TO CO-PENDING APPLICATION

This is a continuation-in-part of Application Ser. No. 09/419,478, filed on Oct. 15, 1999 now U.S. Pat. No. 6,309,217. The subject matter of U.S. Provisional Patent Application Serial No. 60/253,902, filed Nov. 29, 2000 is incorporated herein by reference.

FIELD OF THE INVENTION

The present invention relates to air abrasion devices and, more particularly, to the control of airborne particulate matter produced by such air abrasion devices in operation by the provision of a gas-liquid aerosol.

BACKGROUND OF THE INVENTION

Conventional techniques for repairing or otherwise treating teeth in dental procedures such as the removal of caries or in the manufacture/repair of dental prosthetics (eg. crowns, dentures) typically involve the use of rotary drills. These drills perform at preset speeds; typically "high or "low". As a result, these instruments lack fine control and are imprecise. Furthermore, the drilled surfaces are relatively smooth and accordingly are generally not ideal surfaces for adherence of the metals, porcelains, acrylics and/or composites routinely used in dental practice.

As an alternative to rotary drilling, the use of air abrasion techniques, wherein an abrasive material is conveyed by a rapid air current to impinge forcefully against, and thereby remove through abrasion, unwanted tooth material, is attractive. In the field of micro-dentistry, air abrasion has current but limited use extending to both intra (ie. removal of caries) and extraoral (ie. dental prosthetics) applications. A major advantage of air abrasion in micro-dentistry (AAMD) over conventional rotary drills is that it is more precise and affords the user much more control in the aforementioned intra and extraoral applications. Additionally, AAMD typically results in uneven surface areas which are more amenable to secure receipt of adhesives. Further, anaesthetic is often not required.

Notwithstanding the apparent advantages of AAMD over conventional rotary drilling, the use of the former has been limited by technical and health-related difficulties. Conventional AAMD devices are not capable of controlling airborne emissions of the abrasive material, nor of the abraded material, either inside the mouth of the patient or to the dental operating theatre. Common abrasive materials include sodium hydroxide and aluminum oxide powder of 27.5 to 50.0 microns in particle size which travels easily in ambient air as dust to foul machinery and other instruments within and generally soil the operating theatre. Further, in the case of powdered aluminum oxide, its aluminum content makes it a toxicological risk for Alzheimer's Disease. Meanwhile, the abraded materials may include as a component abraded dental amalgams which can contain toxic constituents such as mercury, such that use of AAMD for amalgam removal is prohibited in certain jurisdictions. This contamination of dental operating theatres persists in current applications despite the use of high efficiency particulate air (HEPA) vacuum systems. Furthermore, extensive use of intraoral latex rubber dams is also necessary to aid in the prevention of inhalation of the respirable aluminum powder by patients, which is also problematic in light of latex-associated asthmatic and respiratory-type reactions. Moreover, as neither prevention technique is particularly efficient or effective, the continuance of exposure to the abrasive material and abraded materials and the attendant potential for health complication(s) remains of concern to both patients and dental professionals.

In addition, although existing AAMD devices are capable of tooth polishing operations, the technology is currently not widely exploited in this application because such operations are typically quite lengthy in duration, and may result in significant operatory contamination as previously described.

It is known in the prior art to surround the abrasive stream with a curtain of water, so as to minimize contamination. An example of such a prior art device is disclosed in U.S. Pat. No. 3,972,123 (Black), issued Aug. 3, 1976. By utilization of sufficient amounts of water, so as to form a continuous curtain surrounding and impinging upon the soluble abrasive stream, airborne contaminants can be controlled, but this may have deleterious affects upon the ability of the technician to view the target area. Further, the volume of water utilized may require significant evacuation efforts with conventional liquid suction systems, impeding the ability of the technician to complete the operation at hand, and adding to the overall discomfort to the patient The device is also intended for the cleaning of teeth, only, and not for use in restoration procedures.

In light of this prior art, the development of an abrasion device that provides improved dust suppression would be considered revolutionary within the field of microdentistry, in that it would create better visibility for the dentist, create healthier conditions, make practical extra and intra-oral usage and eliminate the need for costly high efficiency particulate air (HEPA) filter vacuum units.

Similar benefits and drawbacks as previously discussed apply in relation to the use of known air abrasion devices in medical surgery, for removal of unwanted bone material. (Of course, the concern as to airborne abraded amalgam does not apply in the context of medical surgery, as such amalgams are typically not present.) As well, if an air abrasion device incorporating effective dust suppression technology were produced, same would no doubt find utility in other fields, such as, for example, in tools for arts and crafts, or for use in fine manufacturing operations, for example, in the computer industry.

It is therefore an object of the present invention to provide a novel abrasion device with improved dust suppression.

SUMMARY OF THE INVENTION

In one aspect of the present invention, there is provided an abrasion device comprising a first delivery means for delivering an abrasive material to a target region; a supply means for supplying a fluid, said fluid comprising a gas-liquid aerosol; and a second delivery means for delivering said fluid near said target region under conditions sufficient to suppress airborne emissions of said abrasive material from said target region.

Preferably, the first delivery means includes a head and a nozzle mounted on the head with a first conduit therein to receive the abrasive material. The second delivery means includes a plurality of second conduits near the first conduit to receive the fluid. The second conduits are arranged so that the fluid leaving them generates, for example, a curtain-like stream toward the target region. In other words, the individual fluid streams leaving the second conduits converge to a hollow substantially continuous stream to define an inner region. Conveniently, the first conduit may be arranged to deliver the abrasive material to the inner region. The pressure and content of the fluid can thus retard or, in some cases prevent, airborne abrasive material from breaking through the curtain, either causing it to be entrained in the fluid or to be repelled back into the inner region.

The fluid may be provided in a variety of forms including an aerosol of water and a gas such as air, or other suitable gases such as nontoxic or inert gases, for example, nitrogen or carbon dioxide. The fluid itself may be dispensed, if desired, at pressures ranging from 5 to 75 psi, for example. It is also contemplated that the fluid may comprise disinfectants, so as to reduce the likelihood of operatory infection and to increase communicable disease control.

In another aspect of the present invention, there is provided an abrasion device comprising a first delivery means to deliver abrasive material to a target region and a second delivery means to deliver a supply of a fluid, said fluid comprising a gas-liquid aerosol, near said target region under suitable conditions for retarding the passage of airborne abrasive material therethrough.

Preferably, the fluid forms a curtain around the target region. More preferably, the curtain completely encircles the target region.

In still another aspect of the present invention, there is provided an abrasion device operable to deliver an abrasive material stream to a target region and a fluid stream, said fluid comprising a gas-liquid aerosol, near said target region under conditions sufficient to suppress airborne abrasive material emissions from said target region.

In still another aspect of the present invention, there is provided a method of abrading a target, comprising the steps of delivering a first supply of abrasive material to a target region and delivering a second supply of a gas-liquid aerosol near said target region, wherein said gas-liquid aerosol has sufficient volume and pressure to form a barrier to airborne abrasive material.

Thus, the invention provides an abrasion device that utilizes abrasive dust as the abrasive material, and which provides effective dust suppression by the use of a stream of a gas-liquid aerosol, such as, for example, an air-water aerosol. In this example, the device emits a stream of the abrasive material as well as the air-water aerosol, the latter under conditions sufficient to minimize the amount of dust leaving the target region and thus control widespread contamination by the airborne abrasive material.

The abrasion device may be hand controlled, by way of "push button" or "touch sensory" controls. Furthermore, the controls may be such that the gas-liquid aerosol and the abrasive stream are continuously variable, are regulated in a stepwise manner (ie. highmedium-low), or are controlled in a simple on-off manner. The device may also be used with a foot pedal or other such control mechanisms. The invention may also control the composition of the abrasive material stream and the gas-liquid aerosol, such as pressure, flow rate, temperature and the like. The device can also be made adaptable to operatory compressors, and water and electrical supply outlets as allowed by available technology.

BRIEF DESCRIPTION OF THE DRAWINGS

Several preferred embodiments of the present invention will be provided, by way of example only, with reference to the appended drawings, wherein:

FIG. 6 is a side view of still another handpiece;

FIG. 7 is an assembly view of the handpiece of FIG. 6;

FIG. 14 illustrates cutting depths obtained for the operations plotted in FIG. 13.

DESCRIPTION OF THE PREFERRED EMBODIMENTS

Figure 1:
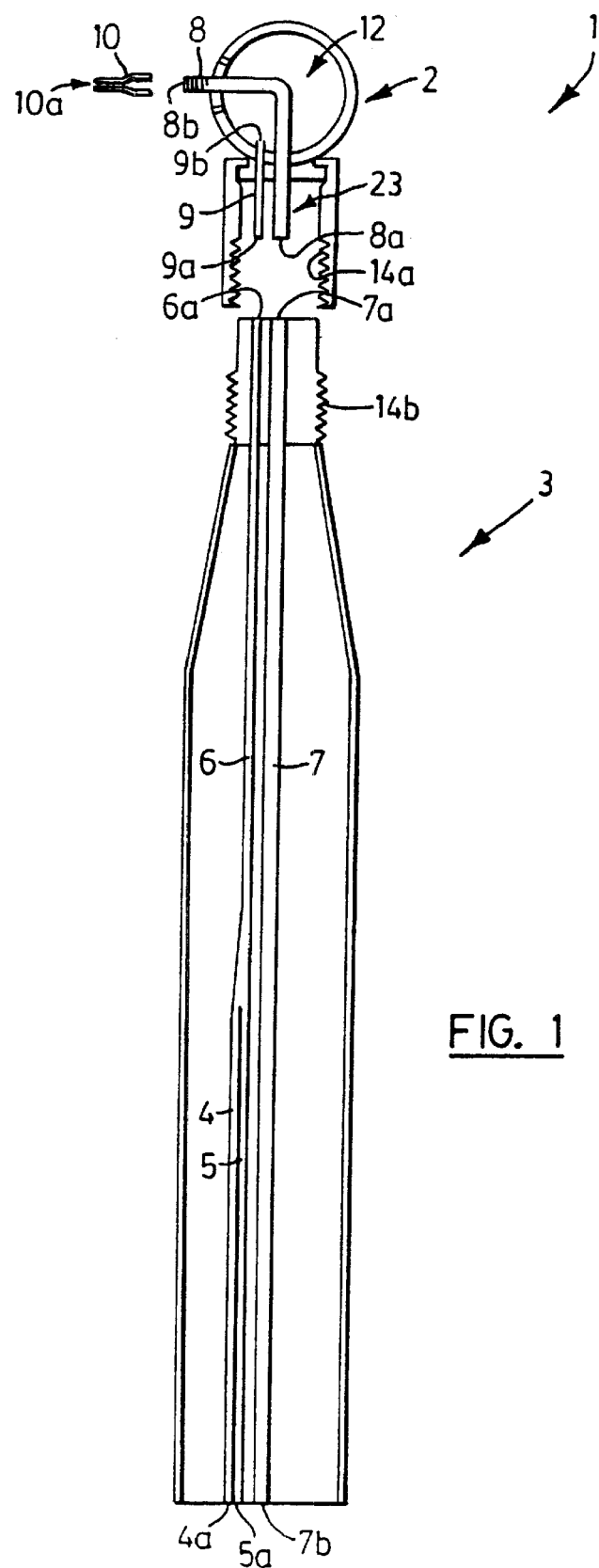
FIG. 1 is a side view of a handpiece of an abrasion device according to a preferred embodiment of the invention.

Referring now to FIG. 1, a handpiece of an abrasion device according to a preferred embodiment of the invention is shown and designated by general reference numeral 1, said handpiece 1 having a head section 2 which is removably attached to a body section 3 by a threaded connection shown at 14a and 14b, it being understood that other attachment modes and means are also feasible. The head section 2 defines a cavity 12 into which a water supply tube 9 opens and across which an abrasive material supply tube 8 extends. A detachable nozzle 10 is affixed to a portion of tube 8 that extends outwards from the head section 2.

Body section 3 is an elongated structure containing a series of tubes 4, 5, 6, and 7 which cross but do not empty internally to body section 3. Tube 7 crosses the entire length of body section 3 and opens externally at either ends of body section 3 at tube openings 7a and 7b. Similarly, tubes 4 and 5 open externally to body section 3 at tube openings 4a and 5a respectively. At a point distal to these tube openings (ie. 4a and 5a) and internal of the body section 3, tubes 4 and 5 merge into a single tube 6. This latter tube 6 opens externally to body section 3 at tube opening 6a. However, it will also be understood that these tubes may be joined at other points both internal and external to the body section. For example, an external control portion may be a convenient place to mix the constituents of the gas-liquid aerosol.

When the head section 2 and the body section 3 are joined or fastened together, tube 9 joins with tube 6 (openings 9a and 6a form a juncture point) and tube 8 joins with tube 7 (openings 8a and 7a form a juncture point). Air may be pumped into tube 4 (through tube opening 4a) and water into tube 5 (through tube opening 5a) or vice versa. The air and water streams combine to form an air-water aerosol at the point in which tubes 4 and 5 merge, and in tube 6 thereafter. This air-water aerosol flows through tube 6, and thence through tube 9 to empty into cavity 12. Abrasive material is streamed under pressure into tube 7 via opening 7b. The abrasive material streams through tube 7 into contiguously joined tube 8 to exit at tube opening 8*b*.

Figure 2:
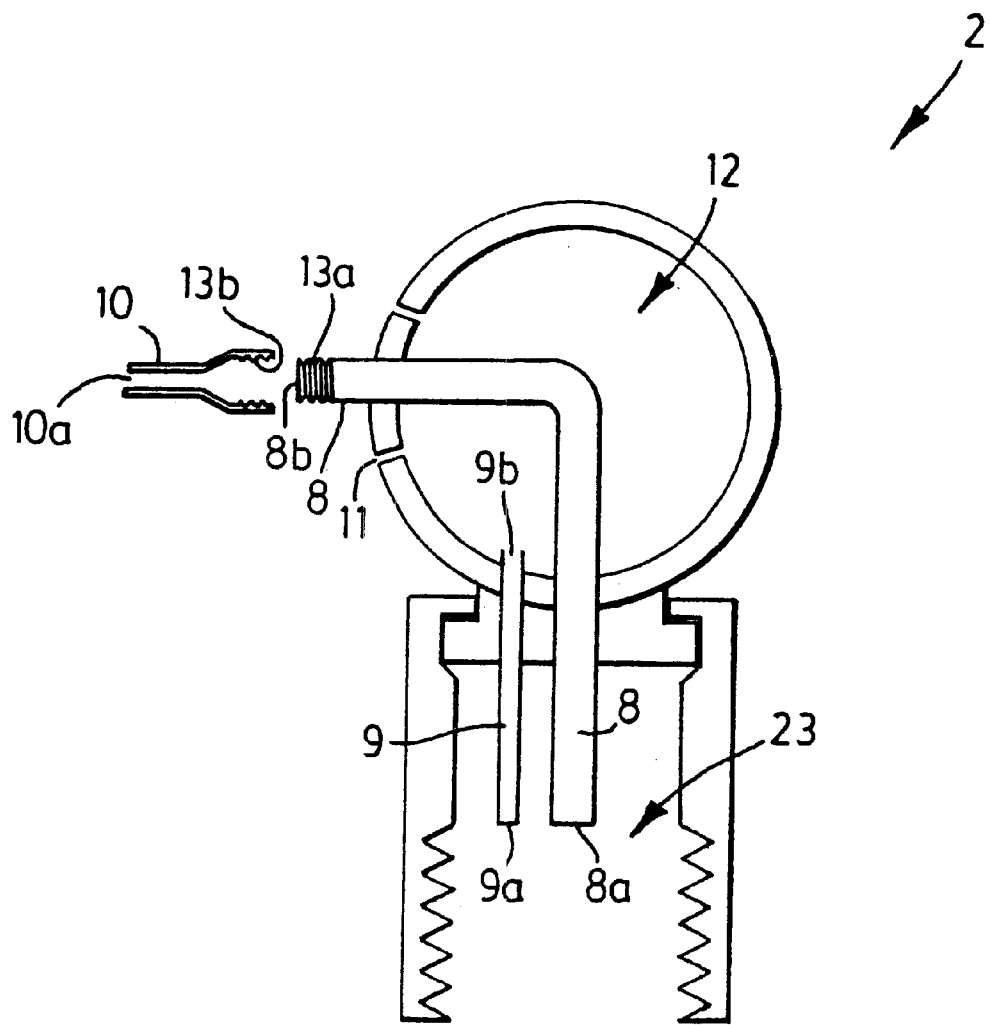
FIG. 2 is a magnified side view of one portion of the handpiece of FIG. 1.

Referring to FIG. 2, a nozzle 10 is further attached to tube 8 via threaded means 13*a* and 13*b*, though it will be understood that other attachment modes and means are feasible. Nozzle 10 opens at some external point (10*a*) to head section 2. This nozzle 10 and its opening 10*a* can be of various sizes and configurations. As previously noted, abrasive material is streamed under pressure through tube 8, to subsequently exit through opening 10*a* of nozzle 10. The air-water aerosol emptying from tube 9 fills cavity 12 of head section 2. The air-water aerosol is channelled through openings 11 of head section 2 to form an airwater aerosol curtain that surrounds nozzle 10. It is the formation of this air-water aerosol curtain that may be configured effectively to control and minimize the widespread contamination of the surroundings by airborne abrasive material emitted through nozzle 10.

Figure 3A:
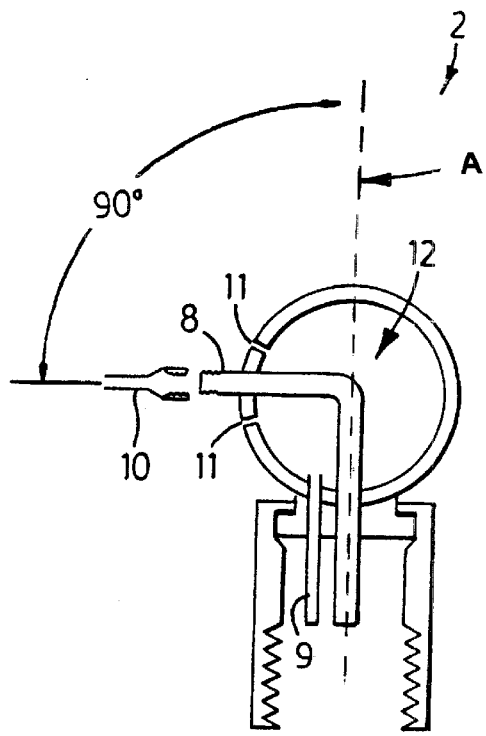
FIGS. 3a to 3d are side views of alternatives to the portion shown in FIG. 2.
Figure 3B:
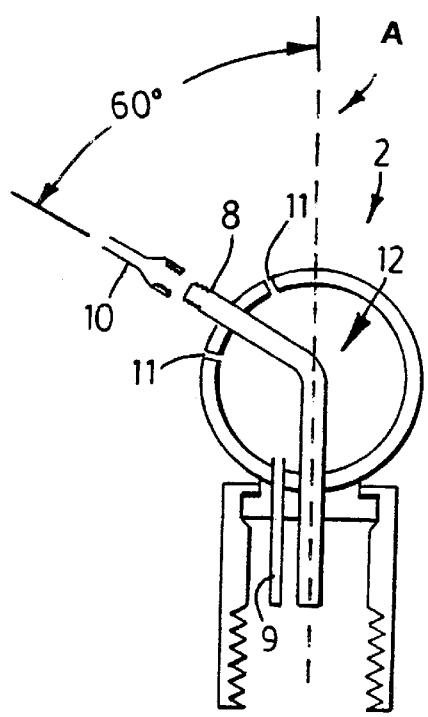
Figure 3D:
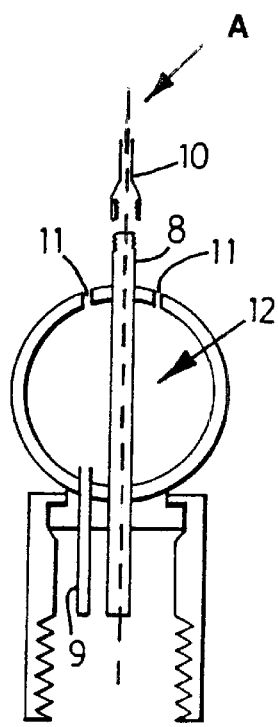
Figure 3C:
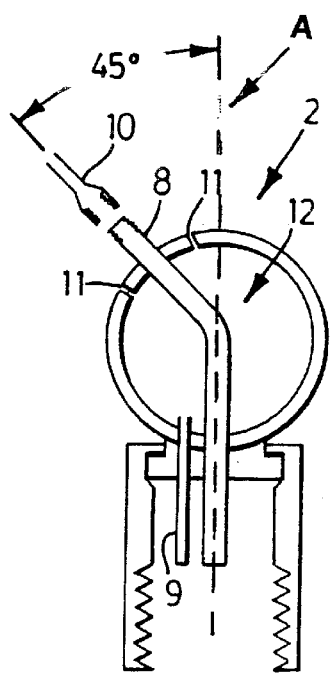

FIGS. 3*a* through 3*d* show alternatives to the head section 2, in which alternatives the tube 8 crosses cavity 12 in a variety of orientations relative to the housing 3. FIG. 3*d*, for example, shows tube 8 crossing cavity 12 so as to extend outward from the head section 2 in substantial alignment with a longitudinal axis A defined by the housing 3. FIG. 3*c*, 3*b* and 3*a* show tube 8 crossing cavity 12 so as to extend outward from the head section 2 at fixed angles of 45°, 60° and 90°, respectively, to axis A. It should be noted that other embodiments are envisioned in which a swivel hinge or mechanism is incorporated in a single head section 2 thus allowing for the variable adjustment of this angle.

Figure 4:
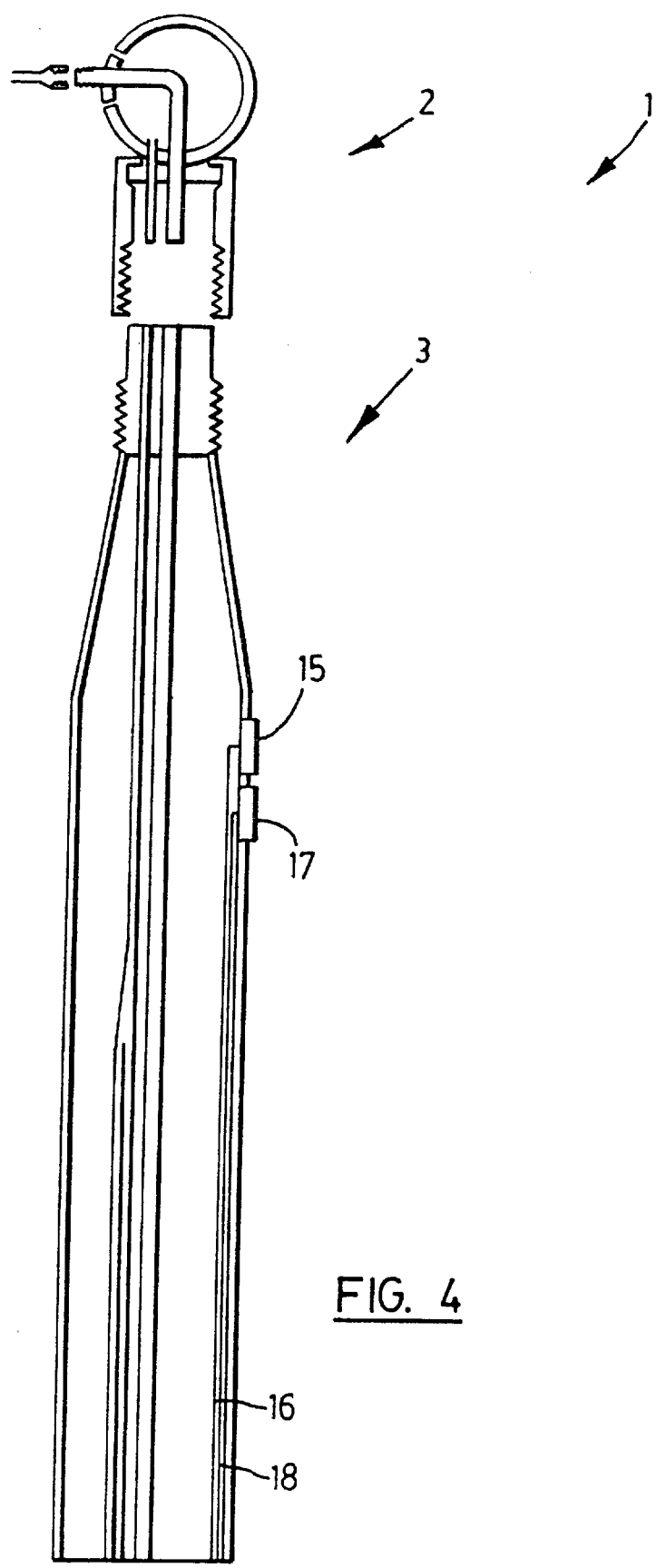
FIGS. 4 and 5 are side views of alternative handpieces.
Figure 5:
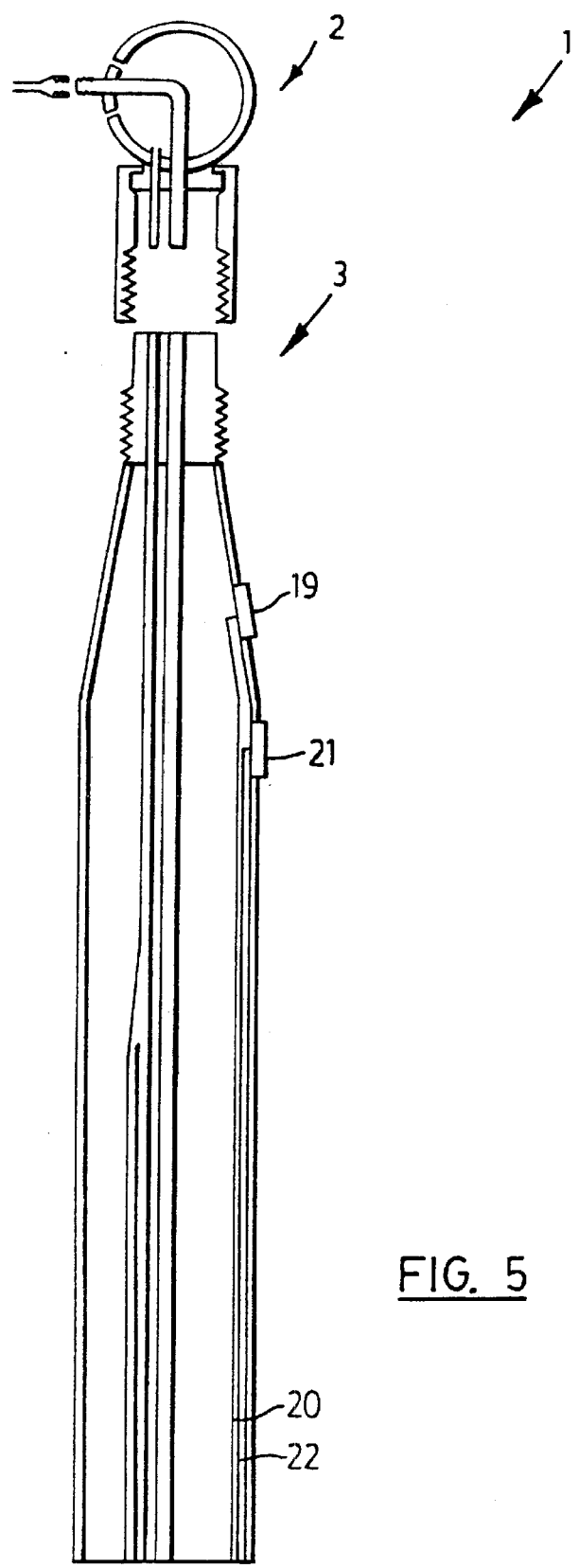

FIG. 4 illustrates an alternative in which the controlling mechanism for regulating the abrasive material stream and the analogous controlling mechanism for regulating the airwater aerosol stream are push-button switches (15 and 17 respectively). These switches function in a simple on-off format. Electrical line 18 supplies electricity to switch 17 and electrical line 16 supplies electricity to switch 15. In the alternative shown in FIG. 5, the controlling mechanism for regulating the abrasive material stream is a touch-control switch 19, while the touch-control switch 21 regulates the water-aerosol stream. These switches are turned on or activated when depressed. Electrical lines 20 and 22 supply power to switches 19 and 21, respectively.

Figure 7A:
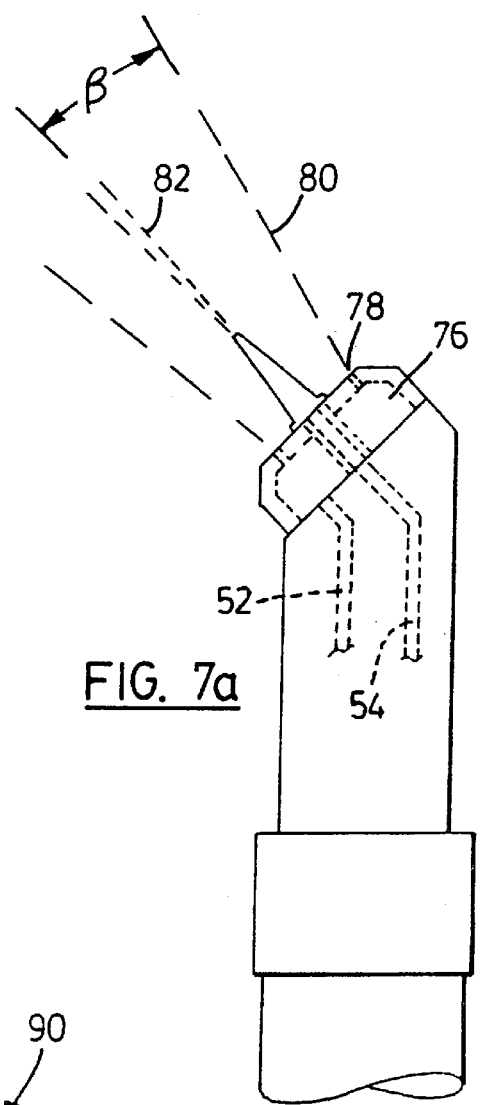
FIG. 7a is a magnified view of a portion of the handpiece of FIG. 6.

FIGS. 6, 7 and 7*a* illustrate another handpiece 40. In this case, the handpiece 40 has a downstream nozzle portion 42 and an upstream body portion 44. The body portion 44 has a central section 46 which is joined to two end sections 48 and 50, each defining downstream and upstream ends 48*a* and 50*a*, respectively. The upstream body portion 44 also has a pair of channels 52, 54 to receive the water-aerosol stream and the abrasive material stream from external supply lines 56 and 58, respectively. The supply lines 56, 58 are suitably mounted in a connector 60 which is coupled to the upstream body portion 44 by a threaded ring 62. The channels 52, 54 extend between the downstream end 48*a* and the upstream end 50*a*. The downstream end 48 a is coupled with the nozzle portion 42 by way of threaded collar 64.

As best illustrated in FIGS. 6 and 7, the nozzle portion 42 includes a main portion 70 with a nozzle body 72 threadably coupled therewith. The nozzle portion 42 also has a nozzle end piece 74 which is threadably coupled with the nozzle body 72.

As best seen in FIG. 7*a*, the nozzle body 72 has a cavity which forms, together with the main portion 70, an inner fluids receiving chamber 76 which is open only to the channel 52 and to a number of conduits, in this case, external orifices shown at 78. Thus, fluids at the entry end of the main portion 70 travel through the channel 52, thence into the chamber 76 and finally through the orifices 78 to form a curtain which is shown by the short dashed lines at 80.

The nozzle portion 42 also forms with the nozzle body 72 a single passage for the abrasive material from the channel 54 through to the nozzle end piece 74, thereby forming a path for the abrasive material through the channel 54, thence through the nozzle end piece 74 and thereafter along the path shown by the dotted lines at 82. In this case, the abrasive material path 82 is centrally located relative to the fluid paths 80 leaving the orifices 78.

The conduits 78 may be provided in a number of configurations including slits or generally circular passages which are oriented to deliver the fluids at an angle β, as shown in FIG. 7*a*, which may range, for example, from 0 to 90 degrees, relative to the abrasive path 82.

Figure 7B:
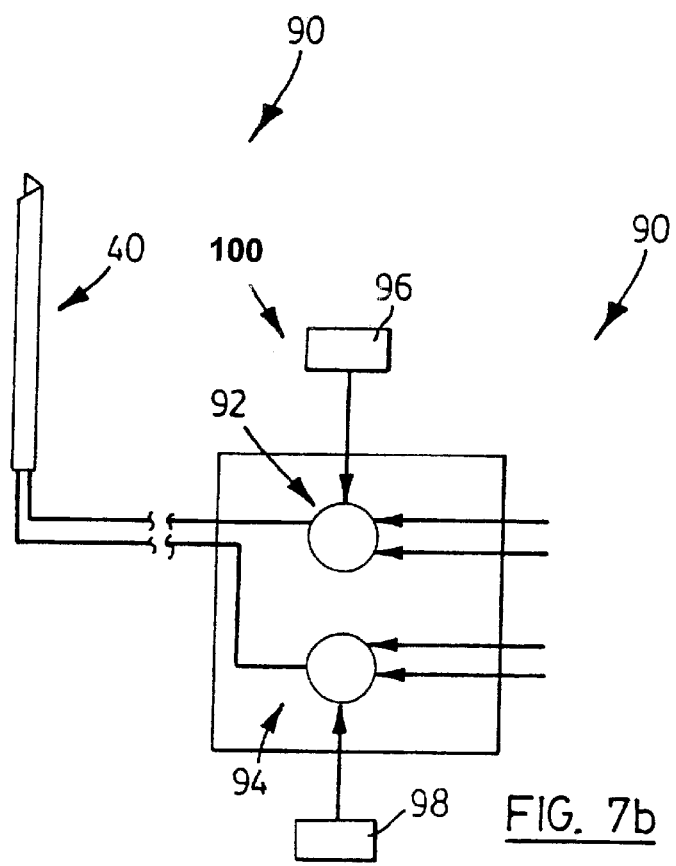
FIG. 7b is a schematic view of an abrasion device according to a preferred embodiment of the invention.

Referring to FIG. 7*b*, the handpiece 40 may form part of an abrasion device 90 which includes an external control portion, designated by general reference numeral 100, which includes a first supply channel 92 to supply a stream of abrasive material and a second supply channel 94 to supply a stream of a gas-liquid aerosol. In this case, the control portion may also include controls 96, 98 to adjust the variables for each stream. The first and second channels may include compressors, mixing chambers, heaters and other means for preparing and conditioning the two streams.

Figure 9:
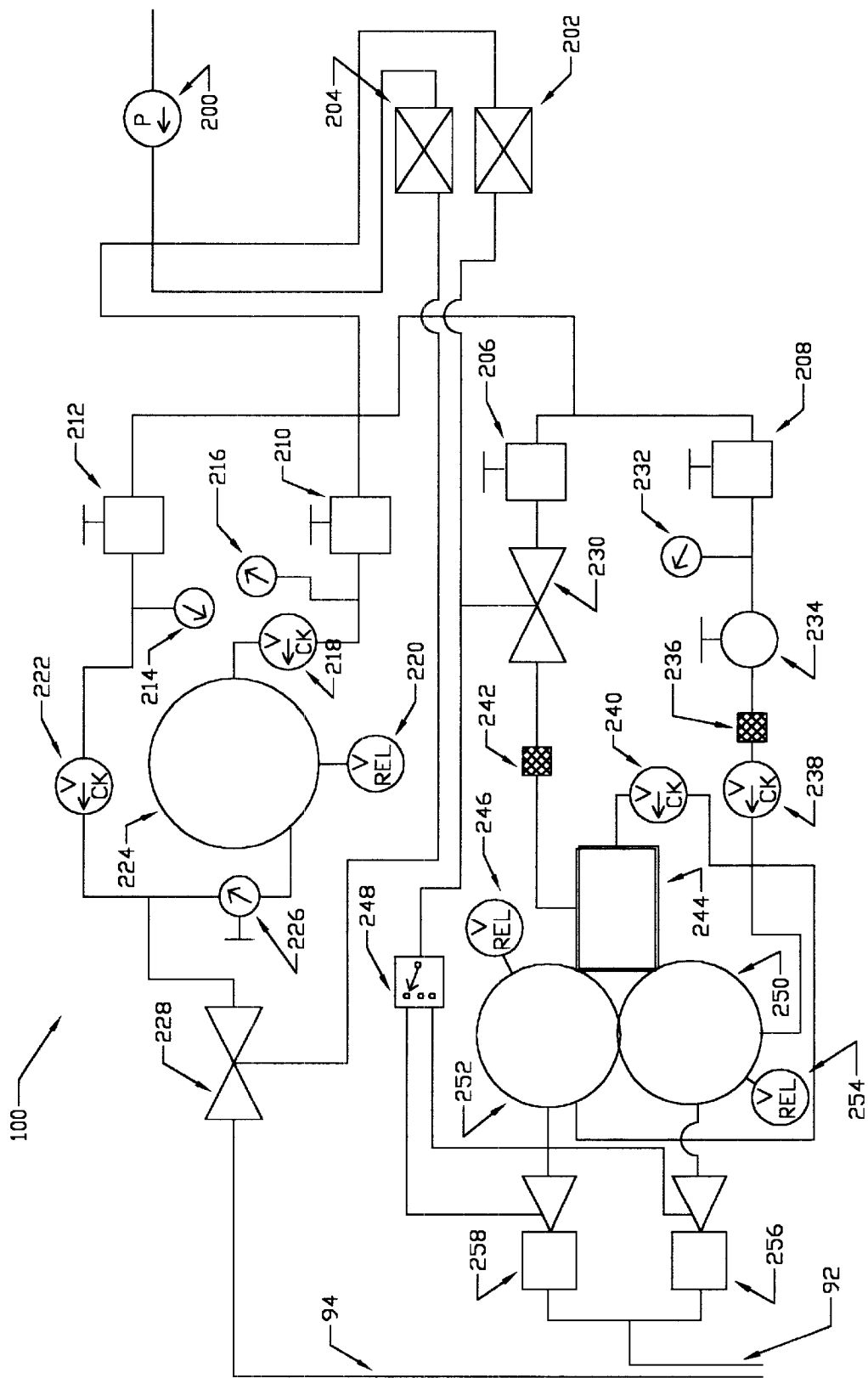
FIG. 9 is a schematic view of the external control portion of an abrasion device according to an alternative preferred embodiment of the invention.

FIG. 9 shows, in schematic form, a preferred embodiment of such an external control portion 100. Said external control portion 100 is seen to comprise an air compressor 200, which is connected to a first foot actuable air valve 204; a second foot actuable air valve 202; a first air pressure regulator 210; and a second air pressure regulator 212; a third air pressure regulator 206; and a fourth air pressure regulator 208. Air delivered by compressor 200 to the third air pressure regulator 206 passes therefrom, at a pressure selected by means of said third air pressure regulator 206, to the inlet of a first pneumatic switch 230. Air delivered by compressor 200 to the first air pressure regulator 210 passes therefrom, at a pressure selected by means of said first air pressure regulator 210, measured by a first air pressure gauge 216, through a second check valve 218 to a liquid reservoir 224, which is itself coupled to the inlet of a second pneumatic switch 228 through a water flowmeter and regulator 226. Air delivered by compressor 200 to the second air pressure regulator 212 passes therefrom, at a pressure selected by means of said second air pressure regulator 212, measured by a second air pressure gauge 214, through a first check valve 222 to the inlet of the second pneumatic switch 228. Air delivered by compressor 200 to the fourth air pressure regulator 208 passes therefrom, at a pressure selected by means of said fourth air pressure regulator 208, measured by a third air pressure gauge 232, through an air flow regulator 234, a second filter 236, a fourth check valve 238, to a first abrasive cannister 252. Air delivered by compressor 200 to the second foot actuable switch 202 passes therefrom to a three position switch 248, for selective passage to the respective trigger of either of a first pneumatic pinch valve 258 or a second pneumatic pinch valve 256. Air delivered by compressor 200 to the second foot actuable switch 202 also passes therefrom to the trigger of the first pneumatic switch 230. Air delivered by compressor 200 to the first foot actuable switch 204 passes therefrom to the trigger of the second pneumatic switch 228. Air leaving the outlet of the first pneumatic switch passes through a first filter 242 to the inlet of a linear vibrator 244, thence through a third check valve 240 to the first abrasive cannister 252 and to a second abrasive cannister 250. The first abrasive cannister 252 is coupled to the inlet of the first pneumatic pinch valve 258. A first pressure release valve 246 is provided for the first abrasive cannister 252. The second abrasive cannister 250 is coupled to the inlet of the second pneumatic pinch valve 256. A second pressure release valve 254 is provided for the second abrasive cannister 250. The first supply channel 92 extends from the outlet of each of the first pneumatic pinch valve 258 and of the second pneumatic pinch valve 256. The second supply channel 94 extends from the outlet of the second pneumatic switch 228.

In operation, activation of the second foot actuable valve 202 triggers the first pneumatic switch 230, allowing air to be passed from the compressor through to the cannisters 250, 252, and also to be passed through the vibrator 244, to agitate the contents of the cannisters 250, 252. Air further passes through to trigger such of the pneumatic pinch valves 258,256 as is selected on the three position switch 248, causing a stream of abrasive material and air to issue through supply channel 92. Different abrasive materials may advantageously be provided in each of the cannisters 252,250, for example, 27 micron and 50 micron aluminum oxide, to allow the technician some variety. Similarly, air leaving from compressor 200 is passed through to the liquid reservoir 224, causing liquid to issue therefrom, and to be mixed with air leaving the first check valve 222 to form an aerosol. The aerosol is selectively permitted egress from the second pneumatic switch 228 upon activation of the first foot actuator valve 204, which passes air to the trigger of said second pneumatic switch 228.

Figure 8A:
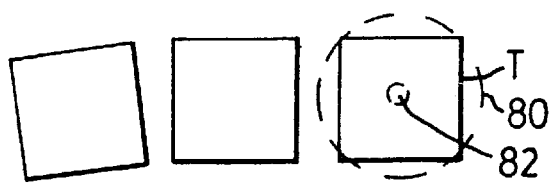
FIGS. 8a through 8e are schematic views of a dental abrading technique.
Figure 8B:
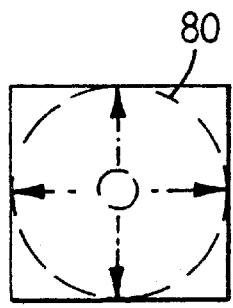

The operation of the tool in AAMD shall now be described with reference to FIGS. 8a to 8e. In FIG. 8a, three teeth are shown schematically by the rectangles 'T'. The abrasive path is shown as the 'bullseye' of a target shown at 82 while the fluid path is shown as a relatively wider circle near the periphery of the tooth T by the dashed lines at 80. While not intending to be bound by theory, it is believed that individual abrasive materials collide with the tooth in the target region and assume random trajectories illustrated, for example, by the four compass-like arrows in FIG. 8b, thereby toward the fluid curtain at the circle 80. As well, it is believed that liberated particles of the abraded tooth material also assume such random trajectories.

Figure 8C:
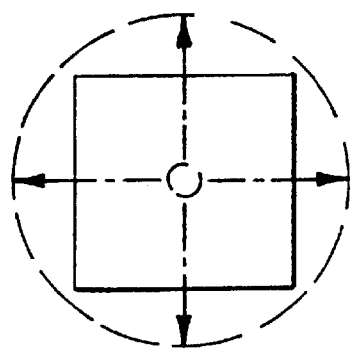
Figure 8D:
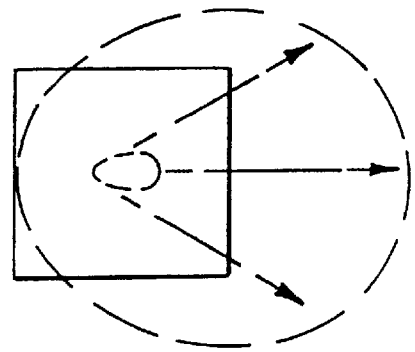
Figure 8E:
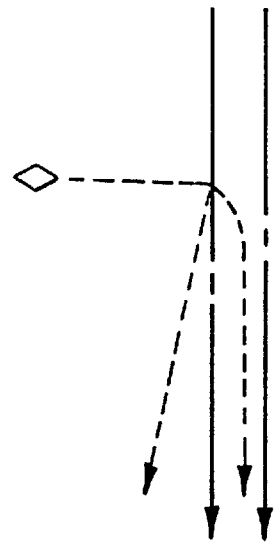

If desired, the curtain 80 may be larger than the periphery of the tooth as shown by FIG. 8c or may take on an ellipsoid-like pattern relative to the tooth, as, for example, might occur if the hand piece is positioned at a smaller angle relative to the tooth. In this latter case, the trajectories of the abrasive materials and liberated particles of the abraded material are shown generally in the right hand direction.

The curtain is in fact a convergence of fluid flows from the individual orifices 78, in this particular example. The fluid will have a momentum which will be dependent on the proportion of the fluid which is a relatively dense material such as water. All other things being equal, the greater the proportion of water in the fluid stream, the greater the chance that the approaching particle of abrasive material or abraded material will collide with or become entrained with an individual droplet in the fluid. This may cause the particle to be repelled back toward the tooth region and thus remain airborne or otherwise be entrained in the fluid.

It will be evident to those skilled in the art that the device will remove material other than tooth material, such as, for example, bone material, surface rust, adhesives for dental crowns, oxides from electrical circuit boards, glass (in glass-etching), etc., in a similar manner, such that a detailed discussion of such operation is not included herein. Further, although the preferred embodiment described contemplates the production of an air-water aerosol, it will also be evident to those skilled in the art that other liquids may be utilized.

While the technique may not in some cases have the capability to inhibit each and every particle of abrasive material or abraded material from actually penetrating the curtain, passing through it and remaining airborne once outside the curtain, it is believed that the technique can be adjusted to provide a very high recapture rate, particularly in respect of fine particulate matter that has the potential to remain airborne for a significant period of time.

The following examples are illustrative of the results that can be achieved by the invention.

EXAMPLE 1

Figure 10:
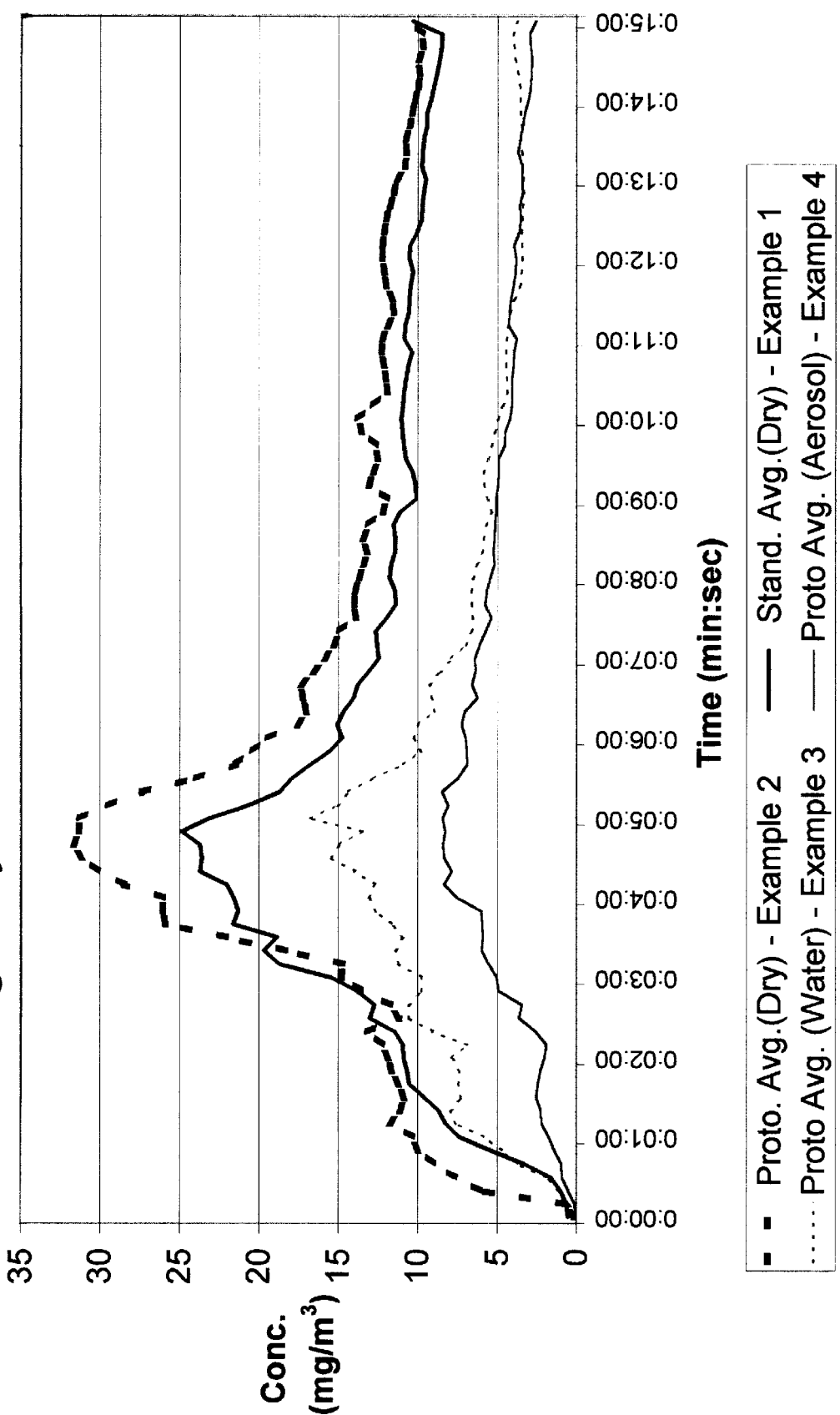
FIG. 10 is a plot of time against particulate concentration for an embodiment of the invention and for devices of the prior art in operation.

In a first test, the hand piece of a conventional air abrasion dental tool sold by American Dental Technologies Inc., of Corpus Christi, Tex. under the trade-mark KCP5 prepjet® and having a nozzle with an internal diameter of 0.38 mm was positioned centrally inside a one cubic metre test chamber; a testing substrate, of the type sold by Whip Mix Corporation of Louisville, under the trade-mark LEARN-A-PREP™, was positioned a measured distance of 2 mm ahead of the nozzle and in perpendicular relation to the outlet thereof; and an aerosol photometer, of the type sold by MIE, Inc., of Bedford, Mass. under the trade-mark MIE personal DataRAM™, was placed within the test chamber a measured distance of 46 cm from the nozzle, said distance being calculated to approximate the proximity of a dental assistant during abrasion operations. Thereafter, 27 micron aluminum oxide, of the type sold by Danville Engineering under stock no. 80042, was ejected through the nozzle by a 100 psig air stream for a five minute period, with photometric measurements being taken throughout that period, and for a further ten minute period, at ten second intervals. Thereafter, the substrate was cleaned, and the depth of the cavity therein produced by the abrasive measured, using a micrometer. The procedure was repeated, with the results of the monitoring being illustrated in FIG. 10, being a plot of mean average concentration of ambient respirable (10 microns or less) aluminum oxide throughout the monitoring period. A time-weighted average, over the first 5 minutes, calculates to 13.2 mg/m$^3$ and, over the complete 15 minute monitoring period, to 12.3 mg/M$^3$ Mean cutting depth was calculated at 4.0 mm.

EXAMPLE 2

In a second test, the hand piece of an air abrasion dental tool constructed in accordance with the teachings of the present invention was positioned centrally inside the test chamber; the LEARN-A-PREP™ testing substrate, was positioned a measured distance of 2 mm ahead of the nozzle of the hand piece and in perpendicular relation to the outlet thereof, which nozzle had a measured internal diameter of 0.375 mm; and the MIE personal DataRAM™ aerosol photometer was placed within the test chamber a measured distance of 46 cm from the nozzle. Thereafter, the powdered aluminum oxide was ejected through the nozzle by a 100 psig air stream for a five minute period, with photometric measurements being taken throughout that period, and for a further ten minute period, at ten second intervals. Thereafter, the substrate was cleaned, and the depth of the cavity therein produced by the abrasive measured, using a micrometer. The procedure was repeated, with the mean average concentration of ambient respirable (10 microns or less) aluminum oxide shown on FIG. 10. A time-weighted average, over the first 5 minutes, calculates to 15.8 mg/m³ and, over the complete 15 minute monitoring period, to 14.8 mg/m³ Mean cutting depth was calculated at 3.7 mm.

EXAMPLE 3

In a third test, the hand piece of Example 2 was positioned centrally inside the test chamber; the LEARN-A-PREP™ testing substrate was positioned a measured distance of 2 mm ahead of the nozzle of the handpiece and in perpendicular relation to the outlet thereof; and the MIE personal DataRAM™ aerosol photometer was placed within the test chamber a measured distance of 46 cm from the nozzle. Thereafter, for a five minute period, the powdered aluminum oxide was ejected through the nozzle by a 100 psig air stream, and simultaneously, water was ejected through the hand piece at line pressure, through five (5) orifices circumferentially spaced about the nozzle, each orifice having a bore of 0.33 mm, being located a measured radial distance of 3.0 mm from the nozzle and a measured distance of 6.0 mm behind the outlet of the nozzle and being oriented at 10° to the abrasive path. Water line pressure varied between 35–50 psig. Photometric measurements were taken throughout the five minute test period, and for a further ten minute period, at ten second intervals. Thereafter, the substrate was cleaned, and the depth of the cavity therein produced by the abrasive measured, using a micrometer. Additionally, the volume of water utilized was measured. The procedure was repeated, with the mean average concentration of ambient respirable (10 microns or less) aluminum oxide throughout the monitoring period being shown in FIG. 10. Mean water utilization was measured at 500 ml. A time-weighted average, over the first 5 minutes, calculates to 9.3 mg/m³ and, over the complete 15 minute monitoring period, to 7.0 mg/m³ Mean cutting depth was calculated at 2.2 mm. The mean average concentration data was smoothed using a least-squares calculation as against a polynomial having the equation $y=cx^b$. The trendline, having an $R^2$ value of 0.8387, is presented on FIG. 13 and discussed in more detail in later paragraphs.

EXAMPLE 4

In a fourth test, the hand piece of Examples 2 and 3 was positioned centrally inside the test chamber; the LEARN-A-PREP™ testing substrate was positioned a measured distance of 2 mm ahead of the nozzle of the handpiece and in perpendicular relation to the outlet thereof; and the MIE personal DataRAM™ aerosol photometer monitor was placed within the test chamber a measured distance of 46 cm from the nozzle. Thereafter, for a five minute period, the powdered aluminum oxide was ejected through the nozzle by a 100 psig air stream, and simultaneously, an air-water aerosol [air delivered at 20 psig; water at line pressure] was ejected through the handpiece, through the five (5) orifices. Photometric measurements were taken throughout the five minute test period, and for a further ten minute period, at ten second intervals. Thereafter, the substrate was cleaned, and the depth of the cavity therein produced by the abrasive measured, using a micrometer. Additionally, the volume of water utilized was measured. The procedure was repeated, with the mean average concentration of ambient respirable (10 microns or less) aluminum oxide throughout the monitoring period being shown in FIG. 10. Mean water utilization was measured at 27 ml. A time-weighted average, over the first 5 minutes, calculates to 4.5 mg/M³ and, over the complete 15 minute monitoring period, to 4.5 mg/m³ Mean cutting depth was calculated at 5.3 mm. The mean average concentration data was smoothed using a least-squares calculation as against a polynomial having the equation $y=cx^b$. The trendline, having an $R^2$ value of 0.9443, is presented on FIG. 13 and discussed in more detail in later paragraphs.

Based on the results of the foregoing testing, it can be seen that the present invention, employing an aerosol curtain, shows a marked decrease in respirable alumina levels in operation as compared to the conventional abrasion tool, and also as compared to a device of similar construction, but utilizing water at like pressure. Indeed, the 15 minute time-weighted averages of the particulate concentrations obtained in Examples 1, 2 and 3, respectively, 12.3, 14.8 and 7 mg/m³, if representative of actual exposures received by persons in the operatory theatres, would approach or exceed the STEL (Short Tern Exposure Limit) of 10 mg/m³ prescribed by the American Conference of Governmental Industrial Hygienists as a maximum for human exposure. In contrast, the 15 minute time-weighted average of the particulate concentrations obtained in Example 4, being 4.5 mg/m³, would fall well-within the STEL values of safety. Moreover, not only are the results obtained in Example 4 superior to those of the prior art, in terms of dust suppression, said results are obtained using a relatively modest amount of water, namely 27 ml, which may be readily removed by occasional deployment of conventional oral evacuation equipment. In contrast, removal of the volume of water utilized in Example 3, namely 500 ml, would require significantly longer deployment of conventional oral evacuation equipment, adding to the discomfort of the patient, and to the complexity of the task faced by the technician. This negative correlation in water utilization as compared to dust suppression is unexpected, and is believed to derive from the presentation of water in aerosol form.

Moreover, even in those cases where relatively coarse and massive particulate material successfully passes through the curtain, such liberated particles should have lost a significant portion of their energy, thereby reducing the velocity of such particles, and thus minimizing the extent of contamination.

Figure 11:
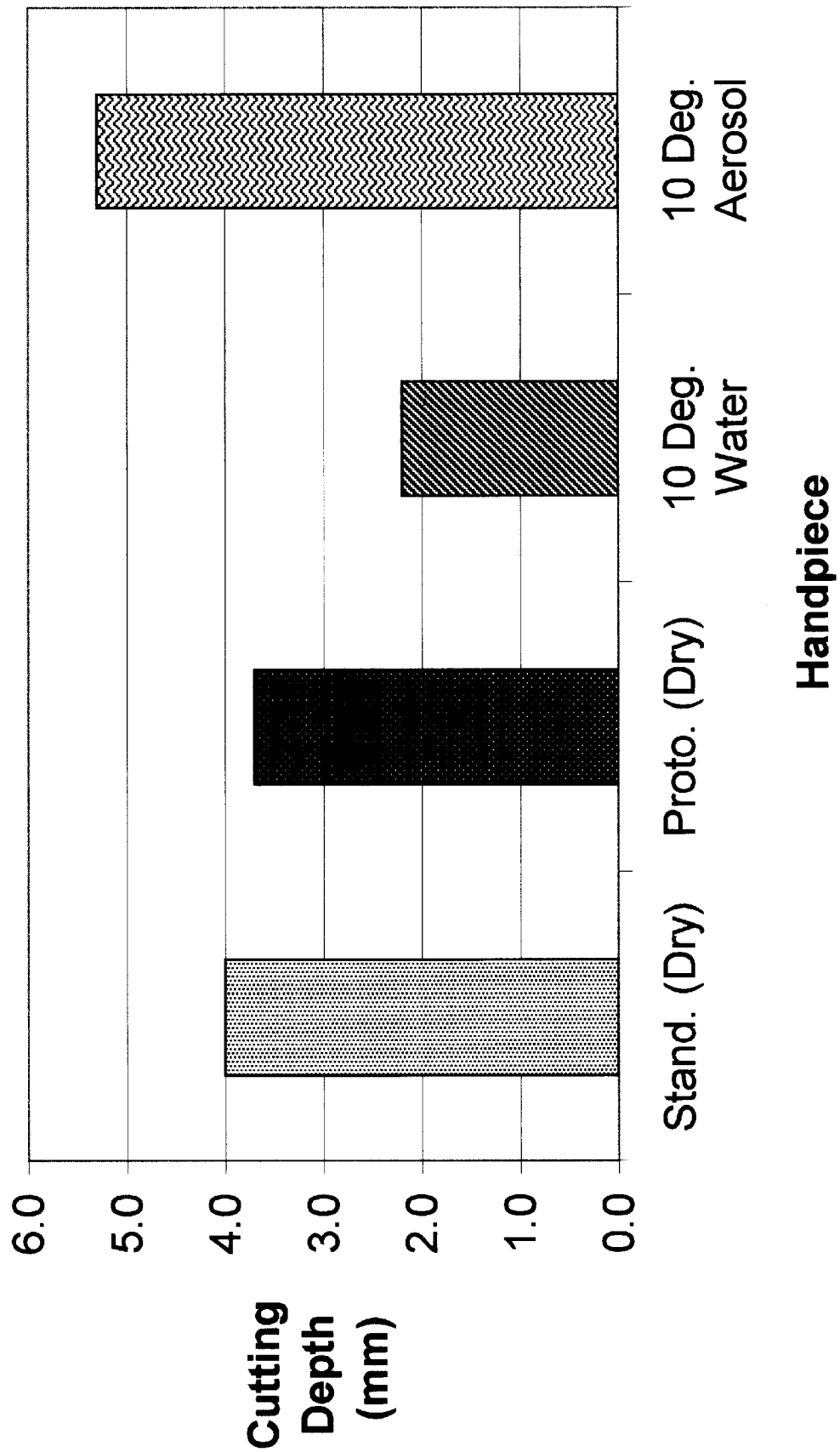
FIG. 11 illustrates cutting depths obtained for the operations plotted in FIG. 10.

A further, unexpected advantage is observed in relation to cutting depths. More particularly, as demonstrated by Examples 2, 3 and 4, which relate to exactly the same tool, and as such, are considered most representative, abrasive cutting depth is observed to be suppressed by the utilization of a water curtain, but increased by the utilization of an aerosol curtain, which is advantageous, in that it enables operations to be completed more expediently, improving the efficiency of the practising technician. This advantage is graphically illustrated in FIG. 11.

Further experiments were undertaken in an effort to quantify the extent of the unexpected advantage in terms of cutting depth that may be obtained by the invention.

EXAMPLE 5

In a fifth test, a hand piece differing from that of Example 4 only in that the orifices were oriented at 0° to the abrasive path was positioned centrally inside the test chamber, the LEARN-A-PREPTM testing substrate was positioned a measured distance of 2 mm ahead of the nozzle of the handpiece and in perpendicular relation to the outlet thereof; and the MIE personal DataRAM™ aerosol photometer was placed within the test chamber a measured distance of 46 cm from the nozzle. Thereafter, for a five minute period, the powdered aluminum oxide was ejected through the nozzle by a 100 psig air stream, and simultaneously, an air-water aerosol was ejected through the handpiece through the five (5) orifices under the same conditions as in Example, 4, namely, air delivered at 20 psig; water delivered at line pressure. Photometric measurements were taken throughout the five minute test period, at ten second intervals. Thereafter, the substrate was cleaned, and the depth of the cavity therein produced by the abrasive measured, using a micrometer. The procedure was repeated, and calculations were made of a mean cutting depth, of 22 mm, and of a 5 minute time-weighted average of particulate matter concentration, at 6.6. mg/m$^3$ Mean water utilization was measured at 27 ml. The mean average concentration data was smoothed using a least-squares calculation as against a polynomial having the equation y=cx$^b$. The trendline, having an R$^2$ value of 0.6805, is presented on FIG. 13 and discussed in more detail in later paragraphs.

EXAMPLE 6

In a sixth test, a hand piece differing from that of Example 4 only in that the orifices were oriented at 5° to the abrasive path was positioned centrally inside the test chamber, the LEARN-A-PREP™ testing substrate was positioned a measured distance of 2 mm ahead of the nozzle of the handpiece and in perpendicular relation to the outlet thereof; and the MIE personal DataRAM™ aerosol photometer was placed within the test chamber a measured distance of 46 cm from the nozzle. Thereafter, for a five minute period, the powdered aluminum oxide was ejected through the nozzle by a 100 psig air stream, and simultaneously, an air-water aerosol was ejected through the handpiece through the five (5) orifices under the same conditions as in Examples 4 and 5. Photometric measurements were taken throughout the five minute test period, at ten second intervals. Thereafter, the substrate was cleaned, and the depth of the cavity therein produced by the abrasive measured, using a micrometer. The procedure was repeated, and calculations were made of a mean cutting depth, of 4.3 mm, and of a 5 minute time-weighted average of particulate matter concentration, at 7.2 mg/m$^3$. Mean water utilization was measured at 27 ml. The mean average concentration data was smoothed using a least-squares calculation as against a polynomial having the equation y=cx$^b$. The trendline, having an R$^2$ value of 0.7638, is presented on FIG. 13 and discussed in more detail in later paragraphs.

EXAMPLE 7

In a seventh test, a hand piece differing from that of Example 4 only in that the orifices were oriented at 15° to the abrasive path was positioned centrally inside the test chamber, the LEARN-A-PREP™ testing substrate was positioned a measured distance of 2 mm ahead of the nozzle of the handpiece and in perpendicular relation to the outlet thereof, and the MIE personal DataRAM™ aerosol photometer was placed within the test chamber a measured distance of 46 cm from the nozzle. Thereafter, for a five minute period, the powdered aluminum oxide was ejected through the nozzle by a 100 psig air stream, and simultaneously, an air-water aerosol was ejected through the handpiece through the five (5) orifices under the same conditions as in Examples 4, 5 and 6. Photometric measurements were taken throughout the five minute test period, at ten second intervals. Thereafter, the substrate was cleaned, and the depth of the cavity therein produced by the abrasive measured, using a micrometer. The procedure was repeated, and calculations were made of a mean cutting depth, of 6.3 mm, and of a 5 minute time-weighted average of particulate matter concentration, at 5.7 mg/m$^3$ Mean water utilization was measured at 27 ml. The mean average concentration data was smoothed using a least-squares calculation as against a polynomial having the equation y=cx$^b$. The trendline, having an R$^2$ value of 0.6976, is presented on FIG. 13 and discussed in more detail in later paragraphs.

EXAMPLE 8

In an eighth test, a hand piece differing from that of Example 4 only in that the orifices were oriented at 20° to the abrasive path was positioned centrally inside the test chamber, the LEARN-A-PREP™ testing substrate was positioned a measured distance of 2 mm ahead of the nozzle of the handpiece and in perpendicular relation to the outlet thereof; and the MIE personal DataRAM™ aerosol photometer was placed within the test chamber a measured distance of 46 cm from the nozzle. Thereafter, for a five minute period, the powdered aluminum oxide was ejected through the nozzle by a 100 psig air stream, and simultaneously, an air-water aerosol was ejected through the handpiece through the five (5) orifices under the same conditions as in Examples 4–7. Photometric measurements were taken throughout the five minute test period, at ten second intervals. Thereafter, the substrate was cleaned, and the depth of the cavity therein produced by the abrasive measured, using a micrometer. The procedure was repeated, and calculations were made of a mean cutting depth, of 4.3 mm, and of a 5 minute time-weighted average of particulate matter concentration, at 6.7 mg/m$^3$. Mean water utilization was measured at 27 ml. The mean average concentration data was smoothed using a least-squares calculation as against a polynomial having the equation y=cx$^b$. The trendline, having an R$^2$ value of 0.4960, is presented on FIG. 13 and discussed in more detail in later paragraphs.

Figure 12:
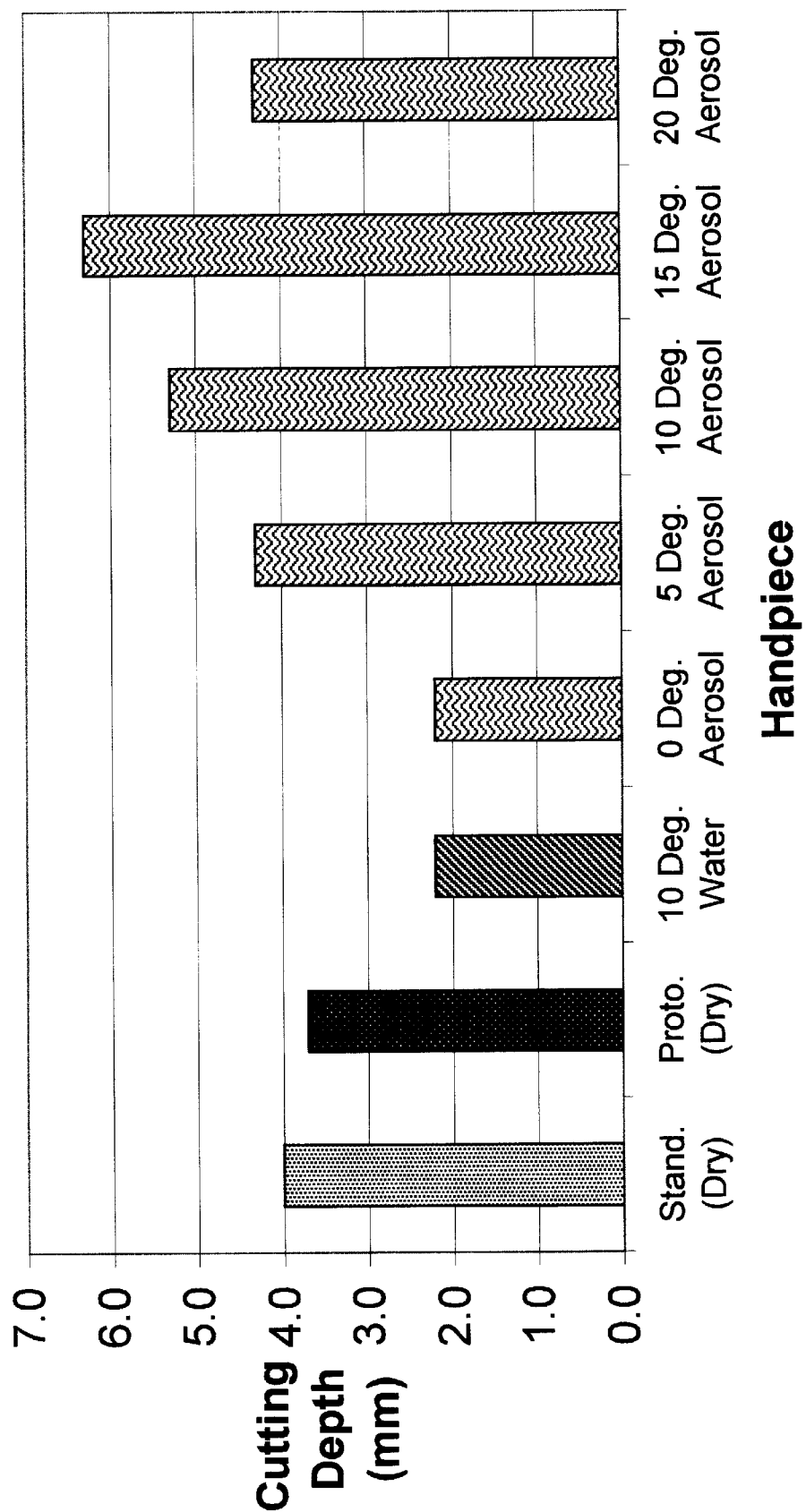
FIG. 12 illustrates cutting depths obtained for various embodiments of the invention in operation, and for devices of the prior art.

The results of the foregoing experiments are shown graphically in FIG. 12. Based on the foregoing results, it will be evident that unexpected improvements in cutting efficiency were obtained in the case of the abrasive tools utilized in Examples 4, 6, 7 and 8, while contemporaneously, providing markedly-improved dust suppression over devices of the prior art (all of the results of the 5 minute time-weighted average (TWA) calculations for such trials, respectively, 4.5, 7.2, 5.7 and 6.7 mg/m$^3$, being superior to those obtained by the prior art devices in Examples 1, 2 and 3, being 13.2, 15.8 and 9.3 mg/m$^3$). The hand piece utilized in Example 5, having orifices orientated parallel to the abrasive path, showed improvement in dust suppression as compared to the conventional abrasion tool (6.6 mg/m$^3$ vs 13.2 mg/m$^3$) but did not offer any improvement in cutting efficiency.

As the experiments demonstrated, in the context of the handpiece of Examples 4–8, that dust suppression properties of the device varied as a function of the orientation of the orifices relative to the abrasive path, further experimentation, under the conditions of Example 3 but with varying orifice orientations was deemed warranted, for control purposes.

EXAMPLE 9

In a ninth test, a hand piece differing from that of Example 3 only in that the orifices were oriented at 0° to the abrasive path was positioned centrally inside the test chamber; the LEARN-A-PREP™ testing substrate was positioned a measured distance of 2 mm ahead of the nozzle of the handpiece and in perpendicular relation to the outlet thereof;

and the MIE, personal DataRAM™ aerosol photometer was placed within the test chamber a measured distance of 46 cm from the nozzle. Thereafter, for a five minute period, the powdered aluminum oxide was ejected through the nozzle by a 100 psig air stream, and simultaneously, water was ejected through the handpiece at line pressure, under the same conditions of Example, 3, through the five (5) orifices. Photometric measurements were taken throughout the five minute test period, at ten second intervals. Thereafter, the substrate was cleaned, and the depth of the cavity therein produced by the abrasive measured, using a micrometer. The procedure was repeated, with a mean cutting depth calculated at 1.3 mm, mean water utilization measured at 500 ml and a five-minute TWA calculated at 14.0 mg/m$^3$. The mean average concentration data was smoothed using a least-squares calculation as against a polynomial having the equation $y=cx^b$. The trendline, having an $R^2$ value of 0.5698, is presented on FIG. 13.

EXAMPLE 10

In a tenth test, a hand piece differing from that of Example 3 only in that the orifices were oriented at 5° to the abrasive path was positioned centrally inside the test chamber; the LEARN-A-PREP™ testing substrate was positioned a measured distance of 2 mm ahead of the nozzle of the handpiece and in perpendicular relation to the outlet thereof; and the MIE personal DataRAM™ aerosol photometer was placed within the test chamber a measured distance of 46 cm from the nozzle. Thereafter, for a five minute period, the powdered aluminum oxide was ejected through the nozzle by a 100 psig air stream, and simultaneously, water was ejected through the hand piece at line pressure, under the same conditions of Example, 3, through the five (5) orifices. Photometric measurements were taken throughout the five minute test period, at ten second intervals. Thereafter, the substrate was cleaned, and the depth of the cavity therein produced by the abrasive measured, using a micrometer. The procedure was repeated, with a mean cutting depth calculated at 1.8 mm, mean water utilization measured at 500 ml and a five-minute TWA calculated at 8.3 mg/m$^3$. The mean average concentration data was smoothed using a least-squares calculation as against a polynomial having the equation $y=cx^b$. The trendline, having an $R^2$ value of 0.7597, is presented on FIG. 13.

EXAMPLE 11

In an eleventh test, a hand piece differing from that of Example 3 only in that the orifices were oriented at 15° to the abrasive path was positioned centrally inside the test chamber; the LEARN-A-PREP° testing substrate was positioned a measured distance of 2 mm ahead of the nozzle of the handpiece and in perpendicular relation to the outlet thereof; and the MIE personalDataRAM™ aerosol photometer was placed within the test chamber a measured distance of 46 cm from the nozzle. Thereafter, for a five minute period, the powdered aluminum oxide was ejected through the nozzle by a 100 psig air stream, and simultaneously, water was ejected through the hand piece at line pressure, under the same conditions of Example, 3, through the five (5) orifices. Photometric measurements were taken throughout the five minute test period, at ten second intervals. Thereafter, the substrate was cleaned, and the depth of the cavity therein produced by the abrasive measured, using a micrometer. The procedure was repeated, with a mean cutting depth calculated at 2.3 mm, a mean water utilization measured at 500 ml and a five-minute TWA calculated at 13.2 mg/m$^3$. The mean average concentration data was smoothed using a least-squares calculation as against a polynomial having the equation $y=cx^b$. The trendline, having an $R^2$ value of 0.8317, is presented on FIG. 13.

EXAMPLE 12

In a twelfth test, a hand piece differing from that of Example 3 only in that the orifices were oriented at 20° to the abrasive path was positioned centrally inside the test chamber; the LEARN-A-PREP™ testing substrate was positioned a measured distance of 2 mm ahead of the nozzle of the handpiece and in perpendicular relation to the outlet thereof, and the MIE personalDataRAM™ aerosol photometer was placed within the test chamber a measured distance of 46 cm from the nozzle. Thereafter, for a five minute period, the powdered aluminum oxide was ejected through the nozzle by a 100 psig air stream, and simultaneously, water was ejected through the hand piece at line pressure, under the same conditions of Example, 3, through the five (5) orifices. Photometric measurements were taken throughout the five minute test period, at ten second intervals. Thereafter, the substrate was cleaned, and the depth of the cavity therein produced by the abrasive measured, using a micrometer. The procedure was repeated, with a mean cutting depth calculated at 2.5 mm, mean water utilization was measured at 500 ml and a five-minute TWA calculated at 14.0 mg/m$^3$. The mean average concentration data was smoothed using a least-squares calculation as against a polynomial having the equation $y=cx^b$. The trendline, having an $R^2$ value of 0.8594, is presented on FIG. 13.

Figure 13:
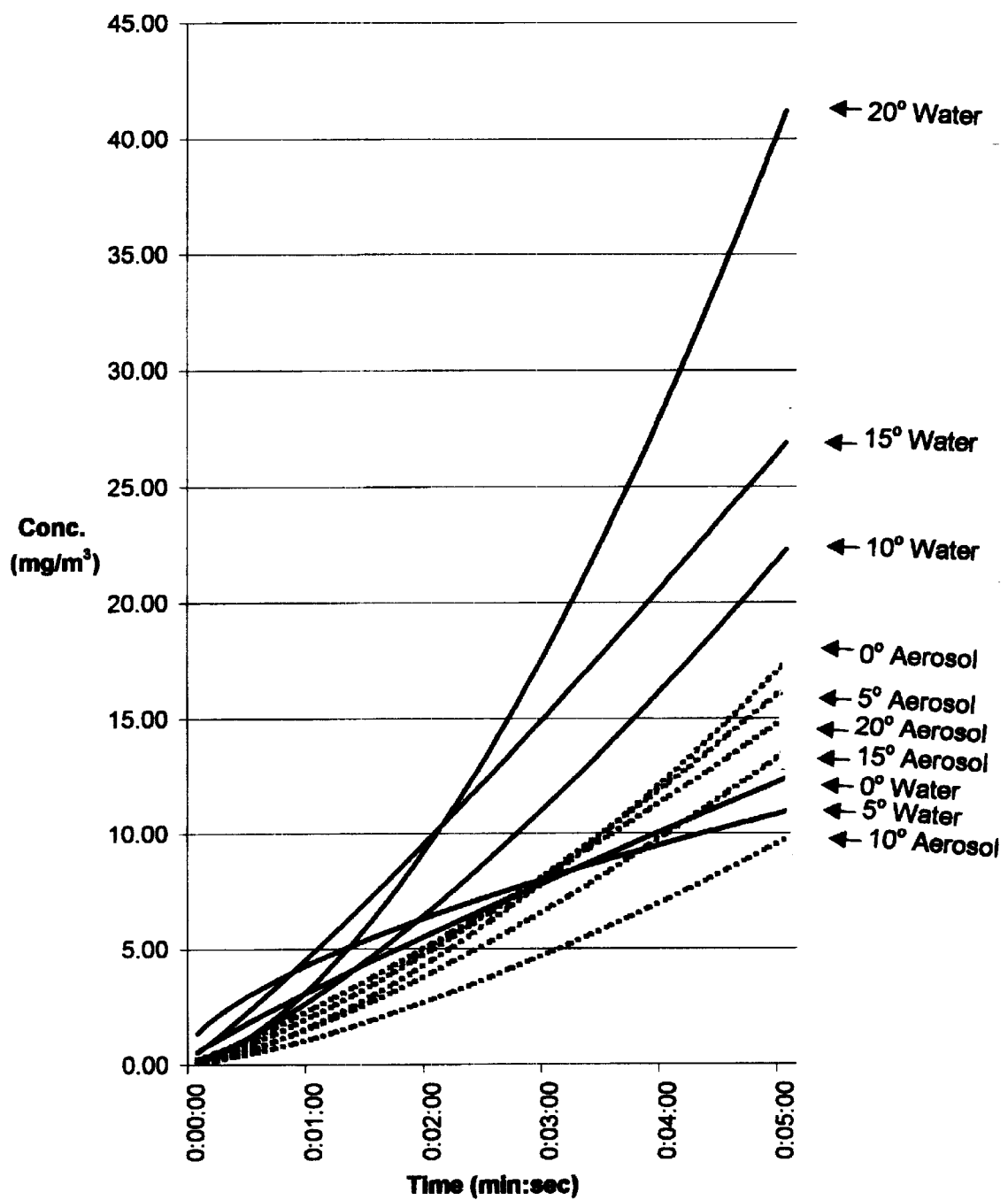
FIG. 13 is a plot of time against particular concentration for various embodiments of the invention and for devices of the prior art in operation.

Having regard to FIG. 13, the trendlines for particulate concentrations for the aerosol device are seen to generally fall beneath those of the water curtain devices of the prior art. The trendlines for the water curtain devices of Examples 9 and 10 [denoted on the Figure as 0° Water and 5° Water] do traverse into the range of the aerosol devices. However, cutting efficiency of the devices of Examples 9 and 10 was observed to be particularly low as compared to the other trials. Significant amounts of water were observed to pool upon the target surface when the water stream was caused to impinge in near perpendicular relation to the target, as was the case in Examples 9 and 10, which pooling was not evident in any of the aerosol trials, nor in the water trials at greater angles. It is postulated that pooling of water caused the deterioration in cutting efficiency, and might well also explain the concentration results, since targeting an abrasive stream at pooled water might be expected to result in a relatively high particulate capture rate. Indeed, this hypothesis is supported by the trendlines, as the $R^2$ values calculated for each of Examples 9 and 10, namely, 0.5698 and 0.7597, are at variance from those of the balance of the water trials (which generally cluster in the 0.83–0.85 range) suggesting a different dust collection mechanism in operation. In any event, it will be evident that the advantage of the present invention over liquid-stream dust suppression devices of the prior art illustrated in FIG. 10, and using far greater volumes of water, was not an anomalous result deriving from a particular inopportune choice of operating parameters in Example 3, but rather, appears intrinsic to the invention, at least in the context of devices having practical utility in cutting.

While not intending to be bound by theory, there are believed to be several variables that are interdependent and changes to them may have positive, or for that matter negative, effects on the ability of the system to suppress airborne materials. For example, increasing the liquid content of the fluid supply, such as water, for example, may improve the dust suppression ability of the fluid, as might an increase in the fluid pressure. An increase in the beam intensity (that is the pressure at which the abrasive material is delivered to the nozzle) may reduce the effectiveness of the fluid curtain, simply because the airborne abrasive materials may penetrate the curtain with a greater speed, for example. However, an increasing content of liquid in the fluid may increasingly impair or obstruct the dental health professional's view of the target region. Therefore, it may be desirable in some cases to permit the professional to adjust these variables at his or her discretion, to allow the system to suppress the airborne material to a degree deemed satisfactory by the professional while at the same time allowing for satisfactory visibility of the target region with a suitable beam intensity.

It will be understood by those skilled in the art that the device should be prepared in a manner suitable for its intended use. This may include, for example, fabricating the device from autoclavable materials or those which are amenable to sterilization by other techniques. It may also be appropriate in some cases to provide the tool as a disposable article.

While the above. system makes use of a tool which supplies both an abrasive material stream and a fluid stream capable of establishing a barrier for suppressing airborne material, the system may alternatively be arranged wherein the abrasive material is supplied by one tool and the barrier-forming fluid stream supplied by another implement.

The terms 'suppress' and 'barrier' are intended not to limit the invention necessarily to only those cases where the suppression and barriers are absolute. Rather, these terms are intended to include cases where the suppression and barriers may only function to prevent a portion of the airborne abrasive material from leaving the target region. For example, there may be significant benefit to be gained by preventing, for example, 90 percent of the airborne materials from leaving the target region.

The device is also convenient because the curtain can be arranged to provide improved suppression without significantly blocking visibility of the target region.

While the curtain shown above completely encircles the target region, there may be cases where the fluid need not form a complete circumferential barrier. For example, there may be some cases where the fluid barrier cooperates with a physical barrier, the latter being, for example the interior surface of the oral cavity of a patient.

The foregoing description of some embodiments of the invention should be considered as merely illustrative of the principles of the invention. Further, since numerous modifications and changes will readily occur to those skilled in the art, it is not desired to limit the invention to the exact construction and operation shown and described. Accordingly, all suitable modifications and equivalents may be resorted to, and are considered as falling within the scope of the invention, including, without limitation, variations in the abrasives chosen, both soluble and insoluble, and also in the components of the aerosol stream.

What is claimed is:

1. An abrasion device comprising a first delivery means for delivering an abrasive material to a target region; a supply means for supplying a fluid, said fluid comprising a gas-liquid aerosol; and a second delivery means for delivering said fluid near said target region under conditions sufficient to suppress airborne emissions of said abrasive material from said target region.

2. A device as defined in claim 1 wherein said first delivery means comprises a head and a nozzle mounted on the head with a first conduit in the nozzle to supply said abrasive material.

3. A device as defined in claim 2, wherein said second delivery means comprises a plurality of second conduits near said first conduit to supply said fluid.

4. A device as defined in claim 3 wherein the second conduits are symmetrically spaced relative to a central axis.

5. A device as defined in claim 4 wherein said first conduit is centrally located relative to said second conduits.

6. A device as defined in claim 5 wherein said second conduits are configured so that individual streams leaving said second conduits converge to a substantially continuous spray of the fluid towards said target region.

7. A device as defined in claim 6 wherein said spray defines an inner region, said first conduit being arranged to deliver the abrasive material to said inner region.

8. A device according to claim 5, wherein the second conduits are orientated to deliver the fluid at an angle ranging from 5 to 20 degrees relative to an abrasive path defined by the first conduit.

9. A device as defined in claim 1 wherein said fluid is an aerosol comprising water and a gas.

10. A device as defined in claim 9 wherein said gas includes air, carbon dioxide or nitrogen.

11. A device as defined in claim 9 wherein the supply means is operable to provide the fluid at a pressure ranging from about 5 psig to 75 psig.

12. An abrasion device comprising a first delivery means for delivering an abrasive material to a target region; a supply means for supplying a fluid, said fluid comprising a gas-liquid aerosol; and a second delivery means for delivering said fluid toward said target region under suitable conditions for retarding the escape of said abrasive material from said target region.

13. A device as defined in claim 12 and which is operable to form a curtain from the fluid around the target region.

14. A device as defined in claim 12 and which is operable to form a curtain from fluid which encircles the target region.

15. A device as defined in claim 12 wherein said first delivery means comprises a head and a nozzle mounted on the head with a first conduit therein to receive said abrasive material and said second delivery means comprises a plurality of second conduits near said first conduit to receive said fluid.

16. A device as defined in claim 15 wherein said gas is air.

17. A method of abrading a target, comprising the steps of delivering a first supply of a gas laden with abrasive particles to a target region and delivering a second supply of a pressurized aerosol of a gas and a liquid towards said target region, wherein said aerosol has sufficient volume and pressure to form a barrier to airborne emissions of said abrasive material from said target region.

18. An abrasion device for use with a flow of gas laden with abrasive particles, a flow of gas and a flow of liquid, said abrasion device comprising:

a body member having formed therein a nozzle and a plurality of orifices spaced about said nozzle;

an abrasive channel having a first end adapted to receive the flow of gas laden with abrasive particles and a second end coupled to the nozzle such that, in use, a stream of abrasive-laden gas issues from the nozzle;

an aerosol channel having a first end adapted to receive the flow of gas and a second end coupled to the orifices such that, in use, a stream of gas flows through the aerosol channel towards the orifices; and aerosol means for receiving the flow of liquid and introducing same into the stream of gas such that fine droplets of said liquid are suspended in said stream of gas before it issues from the orifices and such that said fine droplets of liquid and said stream of gas issue as an aerosol curtain from the orifices under conditions sufficient to suppress passage of abrasive material therethrough.

19. An abrasion according to claim 18, wherein the nozzle defines a central axis and the orifices are spaced about the nozzle in substantially surrounding relation and orientated in angular relation to the central axis such that the girth of the aerosol curtain expands at greater distances from the nozzle.

20. An abrasion device according to claim 19, wherein the orifices are orientated at an angle ranging from 5 to 20 degrees relative to the central axis.

21. An abrasion device according to claim 20, wherein the gas is air and the liquid comprises water.

* * * * *